(12) United States Patent  (10) Patent No.: US 7,776,060 B2
Mooradian et al.  (45) Date of Patent: Aug. 17, 2010

(54) CIRCULAR STAPLER BUTTRESS COMBINATION

(75) Inventors: Daniel L. Mooradian, Eagan, MN (US); B. Nicholas Oray, Woodbury, MN (US); William F. Kuester, Blaine, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 1324 days.

(21) Appl. No.: 10/509,216

(22) PCT Filed: Mar. 21, 2003

(86) PCT No.: PCT/US03/08596

§ 371 (c)(1), (2), (4) Date: Jun. 2, 2005

(87) PCT Pub. No.: WO03/082126

PCT Pub. Date: Oct. 9, 2003

(65) Prior Publication Data

US 2005/0228446 A1  Oct. 13, 2005

Related U.S. Application Data

(63) Continuation-in-part of application No. 10/109,595, filed on Mar. 26, 2002, now Pat. No. 7,128,748.

(51) Int. Cl.
*A61B 17/08* (2006.01)
*A61B 17/10* (2006.01)

(52) U.S. Cl. .................. 606/151; 606/153; 227/180.1

(58) Field of Classification Search ............... 606/151, 606/153, 219, 75, 213; 227/175.1, 179.1, 227/180.1
See application file for complete search history.

(56) References Cited

U.S. PATENT DOCUMENTS 3,953,566 A  4/1976 Gore
4,592,354 A  6/1986 Rothfuss
4,665,917 A  5/1987 Clanton et al.
5,104,025 A  4/1992 Main et al.
5,122,156 A * 6/1992 Granger et al. ............... 606/219

(Continued)

FOREIGN PATENT DOCUMENTS

WO  9838923  9/1998

(Continued)

OTHER PUBLICATIONS

Feil/Lippert/Lozac'h/Palazzini (eds.), "History of Mechanical Stapling", *Atlas of Surgical Stapling*, pp. 3-7; 19-21.
L.E. Smith, "Anastomosis with EEA stapler after colonic resection" *Dis. Colon Rectum* 24, 236 (1981).

*Primary Examiner*—Julian W Woo
(74) *Attorney, Agent, or Firm*—Fredrikson & Byron, P.A.

(57) ABSTRACT

A combination medical device comprising a circular stapler instrument (4) and one or more portions of preformed buttress material (16) adapted to be stably positioned upon the staple cartridge (12) and/or anvil (14) components of the stapler (4) prior or at the time of use. Positioned buttress material(s) (16) are delivered to a tissue site where the circular stapler (4) is actuated to connect previously severed tissue portions. An embodiment of the invention allows tissue portions to be joined without the use of sutures. The buttress material (16) is made up of two regions, one of which serves primarily to secure the buttress material (16) to the stapler (4) prior to actuation, and one of which serves primarily to form the improved seal. The former region is severed and discarded upon activation of the circular stapler (4) to form anastomoses, while the remaining material secures and seals the newly connected tissue. Methods of use and preparation of the buttress material (16) are also described.

43 Claims, 9 Drawing Sheets

U.S. PATENT DOCUMENTS

| | | |
|---|---|---|
| 5,222,963 A | 6/1993 | Brinkerhoff et al. |
| 5,250,058 A | 10/1993 | Miller et al. |
| 5,263,629 A | 11/1993 | Trumbull et al. |
| 5,346,501 A | 9/1994 | Regula et al. |
| 5,468,253 A | 11/1995 | Bezwada et al. |
| 5,503,638 A | 4/1996 | Cooper et al. ............... 623/11 |
| 5,549,628 A | 8/1996 | Cooper et al. ............. 606/220 |
| 5,575,803 A | 11/1996 | Cooper et al. ............. 606/151 |
| 5,713,920 A | 2/1998 | Bezwada et al. |
| 5,752,965 A | 5/1998 | Francis et al. ............. 606/151 |
| 5,782,914 A | 7/1998 | Schankereli ............... 623/11 |
| 5,908,427 A | 6/1999 | McKean et al. |
| 5,964,774 A | 10/1999 | McKean et al. |
| 6,099,551 A | 8/2000 | Gabbay ..................... 606/219 |
| 6,165,217 A | 12/2000 | Hayes |
| 6,273,897 B1 | 8/2001 | Dalessandro et al. ....... 606/139 |
| 6,309,423 B2 | 10/2001 | Hayes |
| 6,312,474 B1 | 11/2001 | Francis et al. ............... 623/23 |
| 6,325,810 B1 | 12/2001 | Hamilton et al. |
| 6,468,313 B1 | 10/2002 | Claeson et al. ........... 623/23.72 |
| 6,503,257 B2 | 1/2003 | Grant et al. |
| 6,503,259 B2 | 1/2003 | Huxel et al. |
| 6,540,758 B1 | 4/2003 | Raza ......................... 606/153 |
| 6,592,597 B2 | 7/2003 | Grant et al. |
| 6,638,285 B2 | 10/2003 | Gabbay |
| 6,656,193 B2 | 12/2003 | Grant et al. |
| 7,128,748 B2 * | 10/2006 | Mooradian et al. ......... 606/151 |
| 2003/0178465 A1 | 9/2003 | Bilotti et al. |
| 2003/0183671 A1 | 10/2003 | Mooradian et al. |
| 2005/0059996 A1 | 3/2005 | Bauman et al. |
| 2005/0059997 A1 | 3/2005 | Bauman et al. |

FOREIGN PATENT DOCUMENTS

| | | |
|---|---|---|
| WO | 9945849 | 9/1999 |
| WO | WO 99/48540 | 9/1999 |
| WO | WO 01/54594 | 8/2001 |
| WO | WO 03/082126 | 10/2003 |
| WO | WO 2005/027983 | 3/2005 |

* cited by examiner

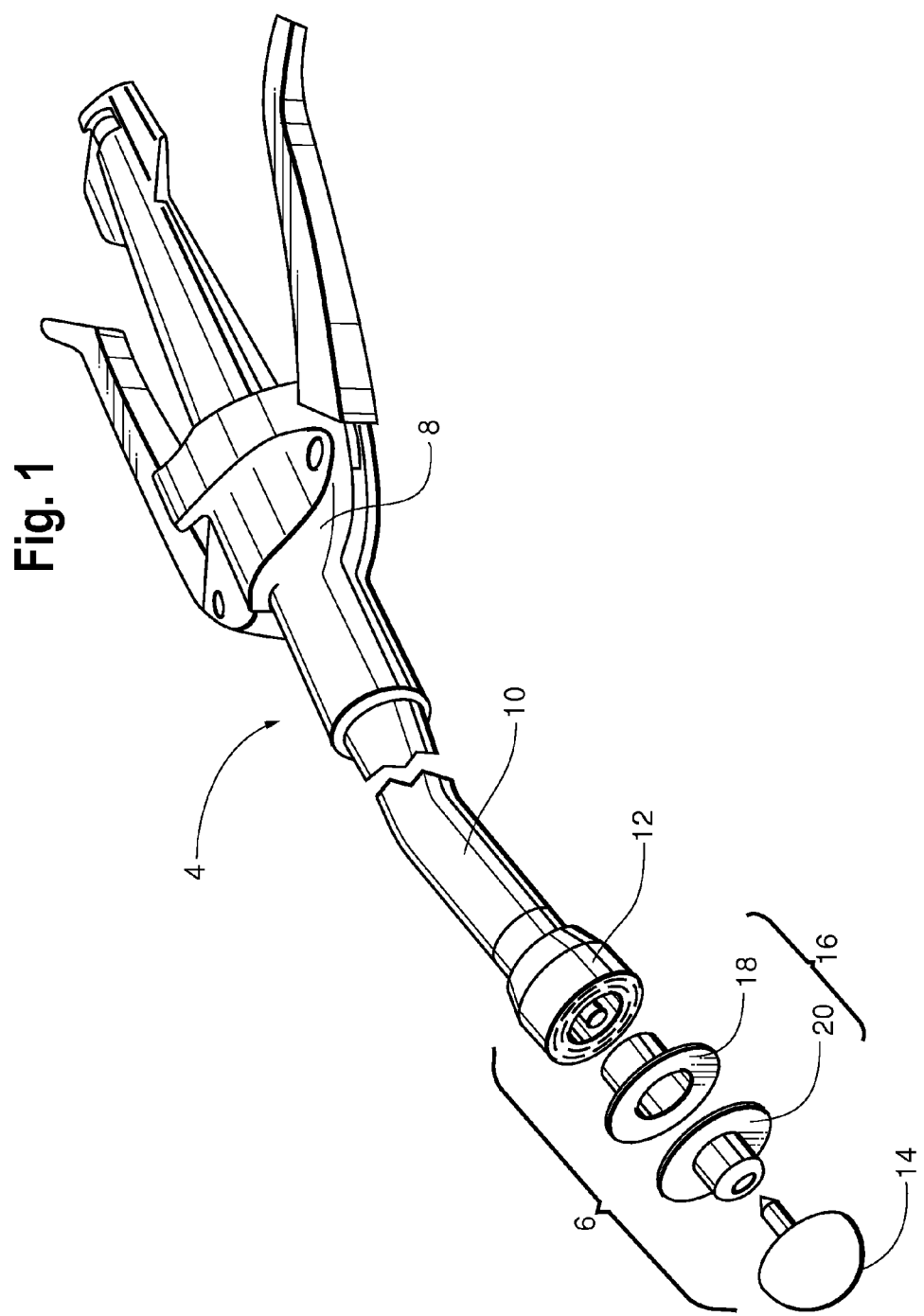

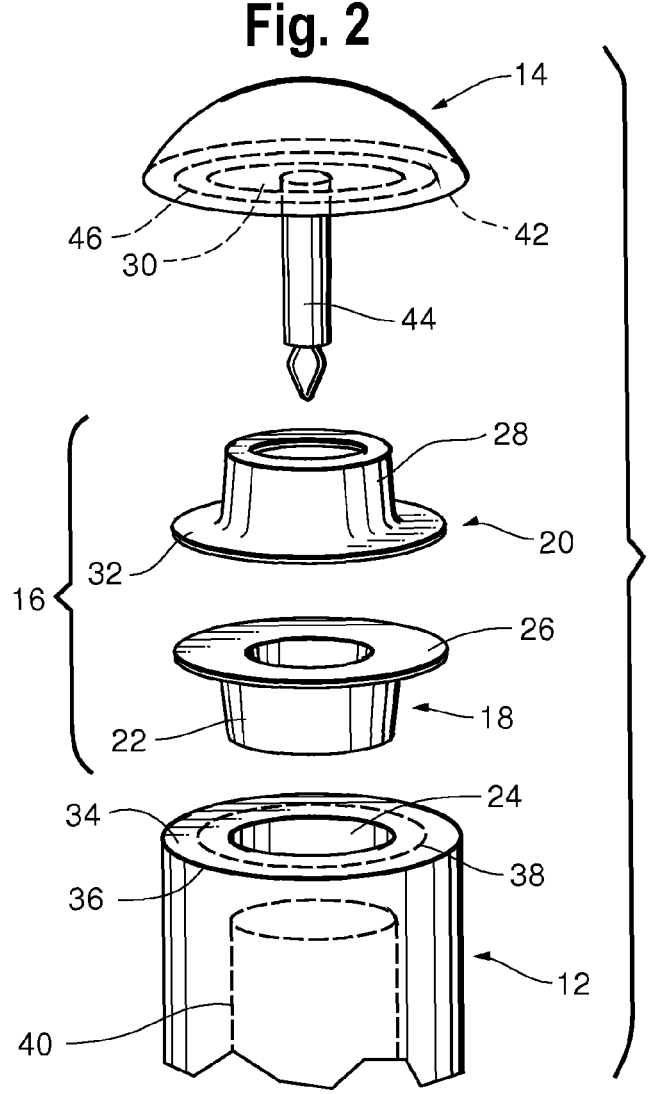
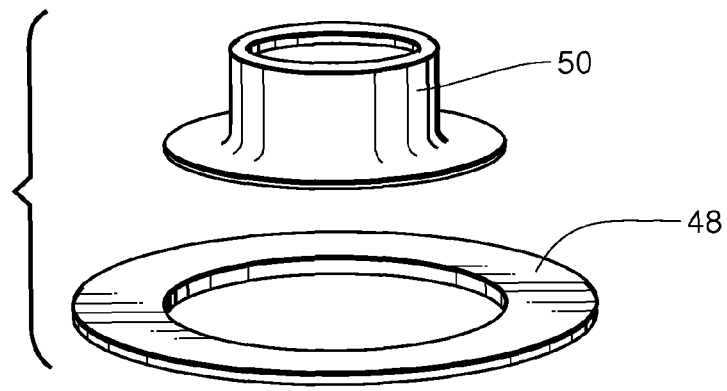

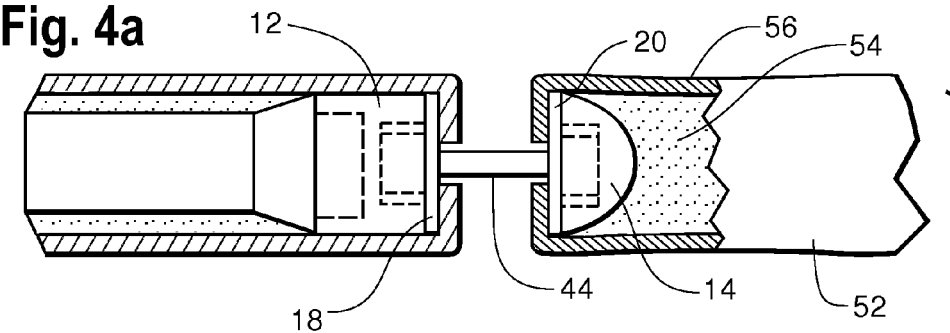
Fig. 4a
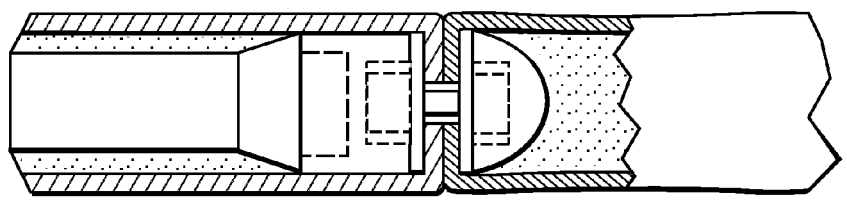
Fig. 4b
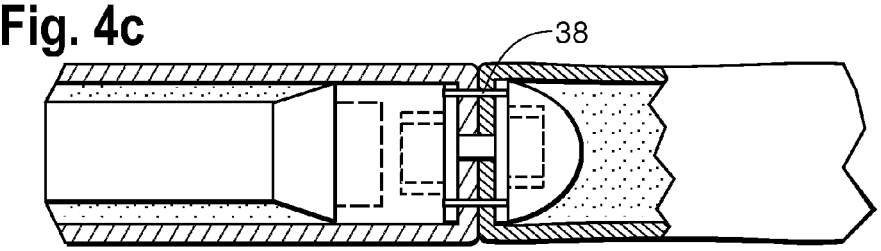
Fig. 4c
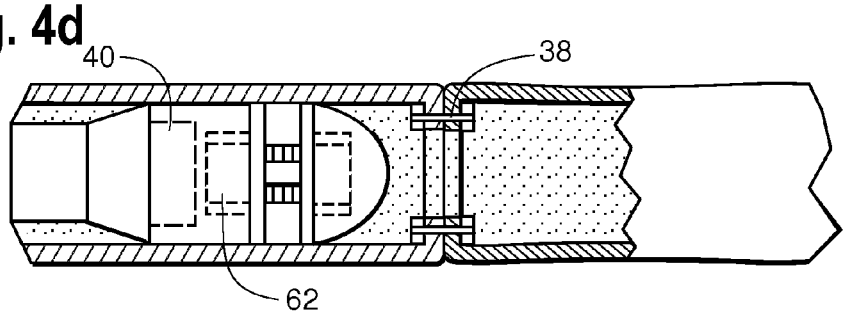
Fig. 4d
Fig. 5
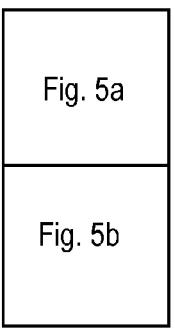

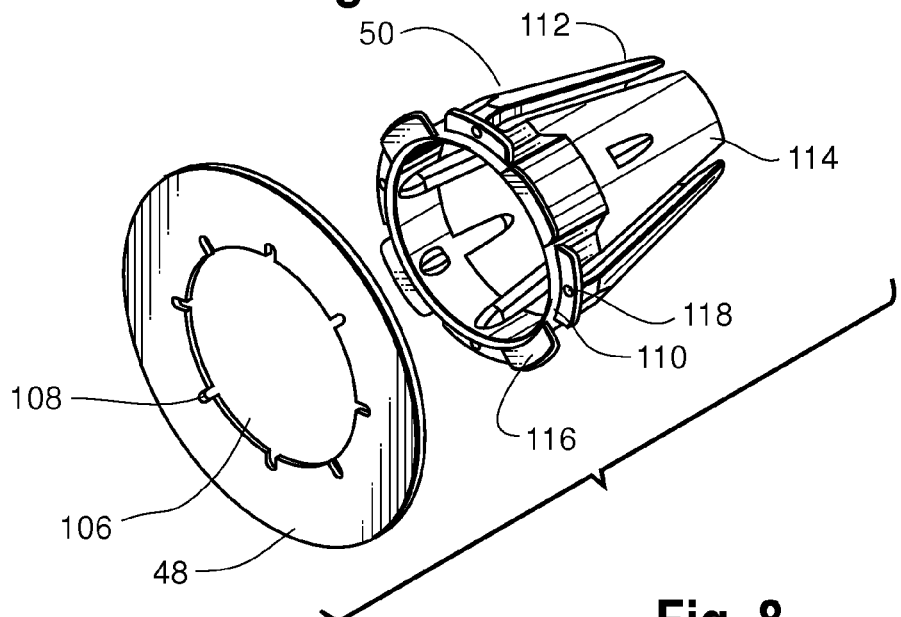
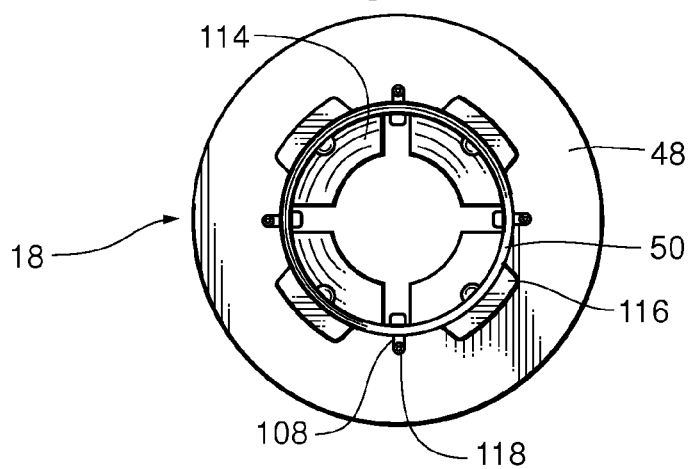
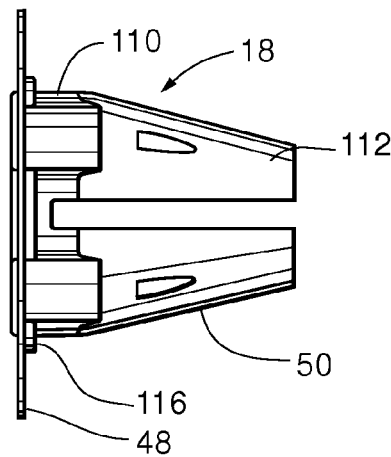

CIRCULAR STAPLER BUTTRESS COMBINATION

CROSS REFERENCE TO RELATED APPLICATIONS

The present application is a continuation-in-part of a U.S. patent application filed Mar. 26, 2002 and assigned Ser. No. 10/109,595, now U.S. Pat. No. 7,128,748 the entire disclosure of which is incorporated herein by reference.

TECHNICAL FIELD

In one aspect, the invention relates to surgical staplers, including circular staplers. In another aspect, the invention relates to surgical stapling procedures that include the use of buttress and reinforcing materials formed of stabilized tissues and polymeric materials. In yet another aspect, the invention relates to the preparation and use of preformed stapler buttress and reinforcing materials for surgical stapling procedures and implantation within the body.

BACKGROUND OF THE INVENTION

Surgical staplers have been used for over a century for providing leak-proof and hemostatic wound closures. See, for instance, "History of Mechanical Stapling", pages 3-7 in Atlas of Surgical Stapling, Feil/Lippert/Lozac'h/Palazzini (eds.). More recently, circular staplers have been developed, having particular use in gastrointestinal surgery to facilitate inverted end-to-end, end-to-side and side-to-side anastomoses. (See pages 19-21, Atlas of Surgical Stapling cited above).

Surgical stapling instruments typically have a mechanism for firing a plurality of staples from a staple-holding cartridge, and an anvil disposed opposite the staple cartridge, against which the staples are formed. Such instruments include, for example, linear staplers, which typically apply one or more parallel rows of staples, and circular staplers, which typically apply one or more concentric and circular rows of staples. In use, the surgeon will place tissue between the staple cartridge and anvil and, by firing the instrument, cause the staples to become clenched to the tissue.

Circular staplers are known and have been successfully used in surgical procedures for many years. Commercially available instruments include the CEEA™ circular stapler, manufactured by United States Surgical Corporation, Norwalk, Conn., and the ILS™ circular stapler, manufactured by Ethicon, Inc., Blue Ash, Ohio. These instruments are typically indicated for use in gastric and esophageal surgery wherein tubular organs are joined to other anatomical structures.

In one common procedure, known as end-to-end anastomosis, a portion of the intestinal tract is removed (i.e., due to the presence of disease such as cancer) and the remaining ends are rejoined by using a circular stapler. To join the tubular structures, one end of intestine is secured about an anvil and the other end of intestine is held in place adjacent to a staple cartridge. Preferably, the anvil has a shaft that is removably connected to the instrument. Once the anvil shaft is secured to the instrument, the anvil is drawn into close approximation to the stapling cartridge. The instrument is then fired to cause the staples to pass through tissue of both organs and become formed against the anvil. During the firing step, a circular knife is advanced to cut tissue inside the staple line, thereby establishing a passage between the organs. After firing, the instrument is typically removed by withdrawing the anvil through the staple line, after which the surgeon will carefully inspect the surgical site to ensure a proper anastomosis (joining) has been achieved.

While circular staplers have been extremely helpful in a number of surgical procedures, when used alone they are prone to creating a number of complications. An early survey of stapler-related complications revealed that in the 3594 end-to-end anastomoses conducted, intraoperative complications were reported in 15.1% of patients and included anastomotic leak, tear during stapler extraction, bleeding, and other complications. L. E. Smith, "Anastomosis with EEA stapler after colonic resection" Dis. Colon Rectum 24, 236 (1981). More recent studies have indicated that postoperative leakage, which can be quite dangerous in gastrointestinal tissue, continues to be a significant problem.

On a different subject, a variety of references teach the preparation of "buttress," "pledget" or "reinforcing" materials for use in combination with conventional surgical staplers. See generally, Applicant's own U.S. Pat. Nos. 5,503,638, 5,549,628, 5,575,803, 5,752,965, 5,782,914 and 6,312,474.

By comparison, relatively few references suggest the use of buttress materials for use with circular staplers. Presumably, this is due to the problems inherent in positioning and using such materials, particularly since neither the shape of a circular stapler, nor the demands of its use, are conducive to the placement or use of conventional buttress materials (e.g., pledgets). For instance, U.S. Pat. No. 6,273,897, which discloses a surgical buttress for use with linear staplers, mentions immediately before the claims that "the present invention may be similarly utilized in conjunction with other types of surgical staplers and cutters. For example, a circular stapler . . . may be suitably modified to provide buttresses on the staple cartridge and the anvil."

On a separate subject, Applicants have previously described the preparation and use of "preformed" tissue implants. See published International Application No. WO 99/48540, the disclosure of which is incorporated herein by reference.

What is clearly needed are materials and methods for providing surgical staple lines, and particularly circular staplers, having improved properties such as staple line strength and buttress seal.

SUMMARY OF THE INVENTION

In one aspect, the present invention provides a combination medical device comprising:
  (a) a circular stapler instrument, comprising a staple cartridge component and corresponding anvil component, and
  (b) one or more portions of buttress material adapted to be a) stably positioned upon the staple cartridge and/or anvil components of the stapler prior to, or at the time of, use, b) while in position upon the stapler component(s), to then be delivered to a tissue site in combination with the stapler components, c) upon delivery of the components and positioned material portion(s) to the tissue site, to provide a first region of buttress material as a staple line buttress seal retained between joined tissue sections upon activation of the stapler, and optionally and preferably, d) to permit the removal of one or more portions of a second region of the buttress material upon activation of a stapler knife provided by the stapler.

The buttress material is adapted to be positioned upon a respective stapler component in a manner sufficient to permit the material to be delivered with the component into the body and to a surgical anastomotic site. By virtue of its physical structure, optionally aided with ancillary materials described herein, the material retains sufficient properties, including shear resistance, to avoid being dislodged or delaminated from its position in the course of positioning.

Optionally, buttress material can include the use of one or more portions of a third region, e.g., axial and external to the second region, for instance in the form of material that extends beyond the rim of a stapler component, and is used to slip fit the material over the component. While it is generally not preferable to include third region portions that would extend beyond the tissue sections being joined (given their tendency to prompt the formation of adhesions within the tissue site), such regions can be provided in a form that permits them to be either removed or biodegraded over time, if desired.

In other aspects, the invention provides a kit comprising preformed buttress material of suitable dimensions to prepare a combination as described above, as well as a method of making and a method of using both the buttress materials themselves and the resultant combination. The buttress material can be provided in dry (e.g., dehydrated) form, or at any suitable stage of hydration. The material can also be packaged separately from the stapler components, or in a manner prepositioned upon the components. Also optionally, positioning of the material upon a respective component can be accomplished or facilitated by the use of ancillary materials, such as gels, ties, or retaining rings.

In a preferred embodiment, the combination comprises a plurality of separate portions of buttress material, wherein each portion comprises material prepared in a manner that permits the material to retain a three dimensional structure corresponding to a respective stapler component. The preformed portions permit the placement and retention of the portions upon respective stapler components, preferably without the need for adhesives, ties, and the like. The preformed portions can be treated (e.g., chemically treated) and/or manipulated (e.g., sewn) to retain suitable three dimensional structure and topographic features (e.g., raised/indented portions, ridges) that permit them to be positioned in a secure fashion upon a respective stapler component, e.g., by press fit or friction fit onto the corresponding grooves, apertures, ridges and edges of the stapler device component. Preferred preformed materials have a "memory" that permits them to retain or assume a predetermined desired shape in the course of use, including in various stages of hydration.

The buttress material portions preferably provide two or more regions, including a first region adapted to remain in position within the body in order to serve as the staple line buttress itself, referred to herein as the reinforcing region, together with one or more portions of a second region adapted to assist in positioning and/or retaining the buttress material upon a stapler component, referred to herein as the positioning region. Preferably, the one or more portions of the second region are adapted to be removed from the tissue site upon activation of the stapler knife. The second region is generally concentric to, and integral with, the first region, the first and second regions cooperating to provide a desired three dimensional and/or topographic structure adapted to position and/or retain the materials in place upon the respective stapler component. Generally, the second region is internal to the circular seam formed, and can be removed together with the severed ends of the joined tissue portions in order to provide an unobstructed lumen for the joined tissue portions.

In one preferred embodiment of the present invention, a buttress material portion can be constructed from a single material. This embodiment will be referred to herein as a homogenous buttress, or homogenous buttress material. In an alternate preferred embodiment, the first and second regions of one or both of the buttress material portions comprise dissimilar materials. This embodiment will be referred to herein as a composite buttress, or composite buttress material. Use of dissimilar materials allows the materials to be optimized for their differing roles as reinforcing or positioning regions, as well as providing other advantages. Two or more dissimilar materials can be used for the various regions of the buttress material portions. These various dissimilar materials can be joined in a variety of ways that will not only provide a union that is suitably strong, but also provide a device that can be more rigid as well as less expensive to manufacture. In a particularly preferred embodiment, the first region of a composite buttress material may comprise non-crosslinked animal tissue, while the second region comprises either crosslinked animal tissue or a polymeric material.

BRIEF DESCRIPTION OF THE DRAWINGS

In the Drawings, wherein like reference numerals are utilized to designate like parts throughout the same:

FIG. 1 is perspective view of a circular stapler, exploded at the distal end, in combination with the buttress material of the present invention;

FIG. 2 is an exploded view in perspective of a circular stapler cartridge and anvil in combination with the buttress material of the present invention;

FIG. 3 is a perspective view of buttress material in which the first and second regions are shown after being severed by a circular knife blade;

FIG. 4 is a schematic view illustrating the technique for stapling abutted tubular tissue sections using the buttress material of the present invention to form an anastomoses;

FIG. 7 is an exploded view in perspective of a composite buttress material for use on the staple portion of a conventional circular surgical stapler;

FIG. 8 is a front view of an assembled composite buttress material of FIG. 7;

FIG. 9 is a side view of the assembled composite buttress material of FIG. 8.

DETAILED DESCRIPTION

Figure 5A:
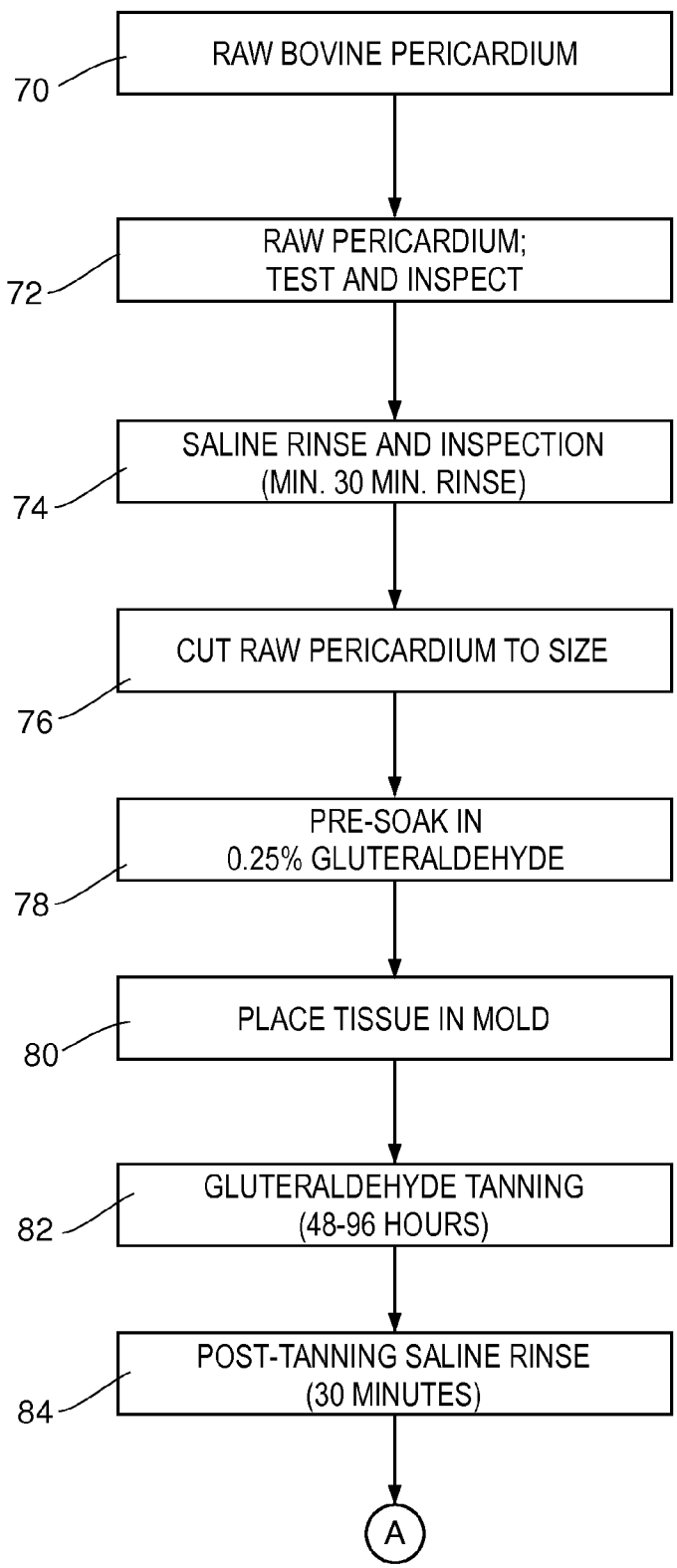
FIG. 5 is a block diagram illustrating a process for the manufacture of one type of homogenous buttress material according to the invention.

Referring to FIG. 1, there is shown a preferred embodiment of a combination device of the present invention, including a circular surgical stapler (4) having a distal fastener head (6), a proximal handle section (8) and an elongated arm connecting the two (10). The proximal handle section allows for positioning of the staple head assembly at the surgical site and bears the controls which trigger the activation of the various components of the distal fastener head. The distal fastener head, mounted on elongated arm (10) at the distal end of the instrument, is composed of two major components, the staple cartridge component (12) and the anvil (14). Buttress material (16) is placed between the staple cartridge component (12) and the anvil (14) and preferably includes two portions; the staple cartridge buttress (18) and the anvil buttress (20), which are secured to the staple cartridge and anvil components, respectively.

Referring to FIG. 2, the combination device of FIG. 1 is shown in more detail by focusing on the distal fastener head (6). As just described, the fastener head has two major components; the staple cartridge component (12) and a corresponding anvil component (14). Also shown is buttress material (16) adapted for use with the circular surgical stapler (4), the buttress including a staple cartridge buttress (18) adapted to be positioned upon the staple cartridge component (12) and an anvil buttress (20) adapted to be positioned upon the anvil component (14).

Connecting the staple cartridge component to the anvil component is the anvil shaft (44). The anvil shaft extends proximally and substantially perpendicular from a plane defined by the staple forming surface of anvil. The anvil shaft is longitudinally movable between a first, extended position and a second, retracted position. In the preferred embodiment, the anvil shaft can be readily detached from the staple cartridge component to allow for easy placement of the buttress component(s).

The staple cartridge buttress (18) is shown having a raised central region (22) that is dimensioned and adapted to be positioned into a recessed aperture (24) within the cartridge component (12), as well as a circumferential flat, disc-like portion (26) adapted to be positioned upon the open face (34) of the staple cartridge component (12), and to ultimately be positioned between the abutted tissue sections (and adjacent to the anvil buttress disc-like portion (32)) in order to serve as a staple line buttress.

The anvil buttress (20) is also shown having a raised central region (28) that is dimensioned and adapted to be positioned into a recessed aperture (30) within the anvil component (14), as well as a circumferential flat, disc-like portion (32) adapted to be positioned upon the open face (42) of the anvil component (14), and to ultimately be positioned between the abutted tissue sections (and adjacent to the staple cartridge buttress disc-like portion (26)) in order to serve as a staple line buttress. Both the staple cartridge buttress (18) and the anvil buttress (20) preferably have an outer diameter at least equal to that of the respective staple cartridge and anvil components.

In a preferred embodiment, the invention provides a surgical stapler combination for joining first and second abutting sections of tissue in order to form a circumferential seam between them. As shown in FIG. 2, the distal fastener head (6) includes a generally cylindrical staple cartridge component (12) comprising a circular face (34) having an outer edge (36), the face and edge being adapted to retain and position a terminal section of the first tissue portion. The stapler also includes a plurality of staples (38) positioned within the face and adapted to be delivered through the positioned tissue upon actuation of the stapler, as well as a generally central aperture (24), and a recessed annular scalpel blade (40) positioned within the central aperture and adapted to be delivered from the cartridge in order to sever an internal circumferential ring of tissue and buttress material.

As shown, the stapler also includes an anvil component (14), mateable with the staple cartridge component (12), and adapted to retain and position a terminal section of the second tissue portion in apposition to the positioned first tissue in the course of a surgical stapling procedure. A typical anvil component (14) has a rounded, conical shape to allow it to pass through tissue more readily. A circular face (42) forms the bottom of the conical shape and is adapted to be positioned and secured to the corresponding circular face of the staple cartridge component. The circular face bears an array of staple-forming grooves (46) adapted to clinch staples delivered through the tissue portions upon actuation of the circular stapler. Finally, the anvil component as shown includes an annular recessed aperture (30) between the conical portion and the circular face, adapted to permit the annular scalpel (40) to fully traverse, and thereby sever, tissue retained between the cartridge and anvil.

With respect to the stapler shown in these Figures, corresponding preformed buttress materials are dimensioned and adapted to be positioned over the circular face of a corresponding stapler component. The buttress materials comprise a generally planar circumferential exterior region (26 and 32) adapted to generally cover the circular face, and in turn, to be positioned between the abutting sections of tissue in order to form a seal therebetween. The buttress materials can be continuous or discontinuous (e.g., as in the form a split washer that would permit them to be slid into position around an anvil stem already positioned within a stapler component.

The buttress materials contain preformed, nonplanar interior circumferential regions (22 and 28) adapted to stably and releaseably position the material upon the face and to thereafter be severed from the buttress device upon delivery of the annular scalpel. FIG. 3 shows the two basic regions of the buttress material(s) following actuation of the stapler and cutting by the scalpel. These include a reinforcing region (48) and a positioning region (50). The reinforcing region (48) is preferably circular and flat, becoming a discrete annulus upon actuation of the stapler. The positioning region (50) is shaped so that it is adapted to be retained in juxtaposition to the stapler component; e.g., to fit within the interior of the stapler component. For example, in one embodiment, the positioning region of the stapler cartridge buttress (22) is generally cylindrical and adapted to position the buttress on the interior surface of the scalpel blade (40) within the stapler cartridge component (12). Preferably, the stapler-buttress combination includes a plurality of preformed buttress materials; for example, it may include buttress materials adapted to be positioned on the anvil and cartridge portions.

The reinforcing region (48) and the positioning region (50) can both comprise a single material, such as animal tissue. This type of buttress is referred to herein as a homogeneous buttress material. Alternately, the two regions can comprise dissimilar materials to create a composite buttress material. The present invention may thus use homogenous buttress materials, composite buttress materials, or a combination of the two in combination with a surgical stapler. An embodiment of composite buttress material used with the stapler component (12) is shown in FIGS. 7-9. FIG. 7 shows an exploded view in perspective of an embodiment of a composite buttress for use on the staple cartridge portion of a conventional stapler, while FIGS. 8 and 9 show front and side views, respectively, of the assembled buttress material. While these Figures show a particular composite buttress in detail, they are merely representative, and a variety of other configurations using two or more regions of dissimilar materials are contemplated within the scope of the present invention.

In the embodiment shown in FIGS. 7-9, the reinforcing region (48) comprises an annular disk, which is substantially flat and contains a central aperture (106) which may contain one or more radially extending notches (108). The positioning region (50) in this embodiment is frustoconical in shape. Like any frustum of a cone, the positioning region (50) has a larger planar end and a smaller planar end, referred to herein respectively as the buttress connector region (110) and the stapler attachment region (112). The cone itself is made up of a plurality of petals (114) which taper axially as they reach the stapler attachment region (112). The capacity of the individual petals (114) to bend allows the positioning region (50) of the composite buttress material to fit snugly within the stapler cartridge (12) component. The positioning region (50) of a composite buttress may be prepared by injection molding, or other suitable means.

The buttress connector region (110) of the composite buttress comprises a plurality of spaced and alternating locking tabs (116), extending radially in an outward direction. Each of the locking tabs (116) has a small dimple projection (118) disposed on its surface and facing inwards, in order to engage and retain reinforcing region (48). To attach the reinforcing region (48) to the positioning region (50) in the embodiment shown in FIGS. 7-9, the positioning region (50) is positioned in a circumferential manner around the aperture of the positioning region (50) in order to engage notches (108) with corresponding dimples (188), thereby ensuring proper orientation and preventing rotational dislocation. The inner edge of the reinforcing region is also press fit between tabs (116) and (118), thereby ensuring a suitably snug fit. In alternate embodiments, the two regions of a composite buttress material may be joined together in a variety of other ways (e.g. by gluing, welding, tacking, adhering, adherence, tacking, tongue-in-groove, or friction fit).

Figure 10:
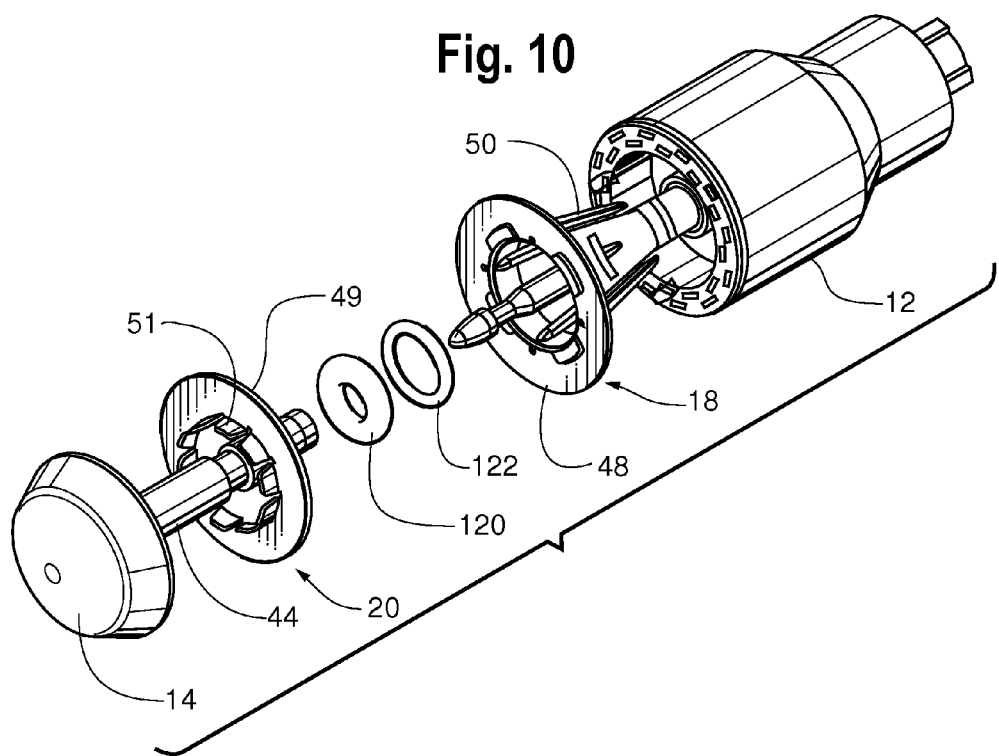
FIG. 10 is an exploded view in perspective of a circular stapler cartridge and anvil in combination with the composite buttress material and placement rings.

Although not shown in isolation, the anvil reinforcing region (49) is adapted to be positioned on the anvil portion of the stapler, and can be prepared entirely from treated tissue or other suitable material. As seen in the context of FIG. 10, anvil reinforcing region (49) is provided as an annular ring having an aperture with integral raised tabs (51) extending distally, toward the anvil surface, and preferably being sufficiently rigidity to retain their orientation. The diameter of the aperture is sufficient to position the buttress material around the anvil shaft, while the outer diameter is sufficient to span the area of the circumferential staple lines. The raised tabs, in turn, permit reinforcing region to extend into whatever aperture (e.g., groove or recess) the open face of the anvil may provide, in order to thereby be sufficiently retained, as by pressure fit.

FIG. 10 illustrates the positioning of buttress materials (18) and (20) within the respective anvil (14) and stapler cartridge (12) components. FIG. 10 further illustrates the positioning of optional retention rings, which can be used to help secure the tissue portions that are being stapled together to the reinforcing regions (48) and (49) of the buttress materials. Preferably, both an anvil retention ring (120) and a cartridge retention ring (122) are used, as shown. In a preferred embodiment of a surgical kit of the present invention, the reinforcing region (48) and the positioning region (50) of a composite buttress for use on the staple cartridge are packaged together, already assembled, and in suitable combination (e.g., kit form) with a corresponding anvil buttress material. The retention rings, on the other hand, are preferably not placed on the composite buttress until they are used during surgery.

Figure 11:
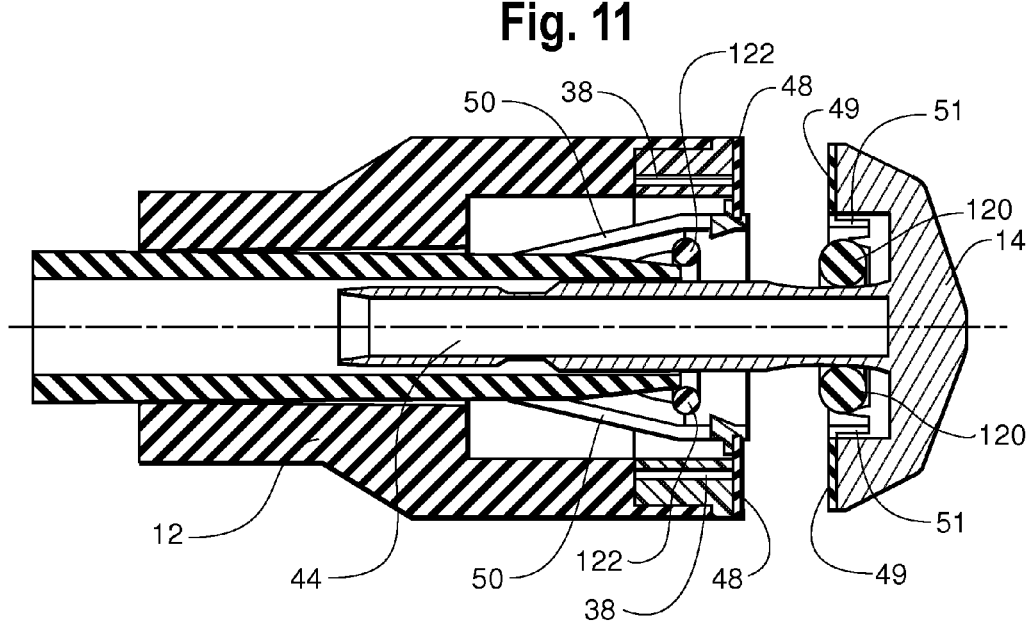
FIG. 11 is a cross section view of a circular stapler cartridge and anvil in combination with the composite buttress material and placement rings.

In one embodiment, the reinforcing regions (48) and (49) can comprise non-crosslinked animal tissue, while the positioning region (50) comprises polymeric material. In a preferred embodiment, the positioning region (50) is constructed so as to be positioned in retained juxtaposition to, e.g., to securely fit, the interior of the staple cartridge component (12) as shown in FIG. 11. This Figure shows the positioning of the retention rings within the staple cartridge component (12) and the staple cartridge anvil (14). Also shown in FIG. 11 are the channels which hold the staples (38) and the anvil shaft (44) which positions and retains the anvil (14) upon the staple cartridge component (12).

Examples of polymeric materials suitable for use in composite buttress materials include one or more polymeric materials selected from the group consisting of polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof. See generally, "Plastics," pp. 462-464, in *Concise Encyclopedia of Polymer Science and Engineering*, Kroschwitz, ed., John Wiley and Sons, 1990, the disclosure of which is incorporated herein by reference. In a preferred embodiment, the positioning region comprises polyethylene. Through the use of dissimilar materials, the properties of the two regions can be more closely tailored to their desired function.

With a composite buttress material, the use of a more rigid material for the positioning region (50) provides a number of advantages. First, it allows the creation of a buttress that is more easily handled and less expensive to manufacture. Second, a more rigid positioning region (50) facilitates improved surgical procedures, such as a sutureless process that avoids the current need to use "purse-string" sutures to hold together adjacent tissue portions, particularly when retention rings are used. Purse string sutures are surgical sutures comprising a running stitch (continuous and inverted) in and out along the edge of a circular wound. The retention rings help hold tissue in place for an anastomoses by assisting in retaining the cut tissue ends over the reinforcing buttress regions. Retention rings are preferably fabricated from an elastomer, with silicon being a particularly preferred material. Provision of a rigid positioning region allows the use of less rigid material for the reinforcing region, while still providing a material that retains its shape and is readily positioned on stapler components.

In a preferred embodiment of the composite buttress material, either crosslinked or non-crosslinked animal tissue can be used for the reinforcing regions (48) and (49), with non-crosslinked animal tissue being particularly preferred. The preparation of non-crosslinked animal tissue suitable for use in the present invention is described in Applicant's own U.S. Pat. No. 6,312,474, the disclosure of which is incorporated herein by reference.

Non-crosslinked, decellularized and purified mammalian tissue (e.g. bovine pericardium) can be used to provide buttress material, including portions thereof, that is both resorbable and remodelable. The material can be prepared by alkylating the primary amine groups of natural tissue in a manner sufficient to reduce the antigenicity of the tissue, and in turn, to an extent that permits the treated tissue to be used in vivo and without crosslinking, thereby permitting it to be resorbable. While not intending to be bound by theory, remodeling appears to occur by gradual bodily processes in which substantial portions of the implant material are gradually resorbed, while an inherent fibrous network of the material is retained at the site. This network, in turn, can be used by the body as scaffolding for the generation of new tissue. Such material leads to the formation of an excellent seal between joined tissues in anastomotic procedures, while preventing adverse bodily reactions such as adhesion formation.

The combination of this invention can include any suitable surgical instrument for applying a circular array of fasteners, e.g., staples. Examples of suitable instruments are found, for instance, in U.S. Pat. Nos. 5,411,508, 5,558,579, and 6,102,271, the disclosures of which are incorporated herein by reference. See FIG. 1 for an example circular stapler. Such instruments typically include a proximal handle section (8) and a distal fastener head (6) connected by an elongated arm (10). Throughout this description, the term "proximal" refers to the end of the apparatus closest to the operator, while the term "distal" refers to the end furthest from the operator. The handle section (8) includes various controls and levers for the operation of the instrument.

FIG. 4 shows a cross-section view of the overall process of creating a reinforced stapled connection between two tubular tissue sections in four steps, from top to bottom, using a preferred embodiment of this invention. In the first step, two ends of tubular tissue (52) are positioned over the ends of the staple cartridge component (12) and the anvil component (14) respectively. The cross section of the tubular tissue wall (56) as well as the interior surface of the tubular tissue (54) are shown. The tubular tissue is typically sutured to hold it in place over the stapler components when homogenous buttress material is used, but other means of holding tissue in place, such as retention rings, are contemplated within the scope of the present invention. The stapler cartridge component (12) and the anvil component (14) are connected by means of the anvil shaft (44). The staple cartridge buttress (18) and the anvil buttress (20) can be seen positioned over and within their respective stapler components. Once the tubular tissue has been properly positioned, the anvil component is moved from the open position spaced away from the staple cartridge component to the closed position, in which the two components are adjacent with tissue and buttress materials sandwiched between them. This is shown in the second step of the procedure.

In the third step, firing of the instrument is generally accomplished by squeezing fastener firing levers present on the proximal handle section (8), as is known in the art, causing staples (38) to be ejected through tissue (56) and buttress material (18 & 20), and into contact with the corresponding anvil component (14). Upon completion of the firing stroke, staples (38) are fully formed against grooves (46) present in the anvil component. Simultaneously, or thereafter, the distal end of an annular scalpel (40) is extended through the sandwiched tissue and buttress material, until it bottoms out in a recessed annular ring within the anvil, thereby severing an inner ring of the sandwiched tissue/buttress material. The annular scalpel (40), grooves (46) and aperture (24) are shown in FIG. 2. The severed material (62) is captured within the aperture (24) of the staple cartridge component (12) and removed along with the distal fastener head, as shown in the last step of FIG. 4. Once the surgical procedure has been successfully completed, a clean cut line, an annular array of staples as well, and at least one piece of buttress material holding the two previously un-joined tissue portions together, form a secure and sealed anastomoses.

Figure 12:
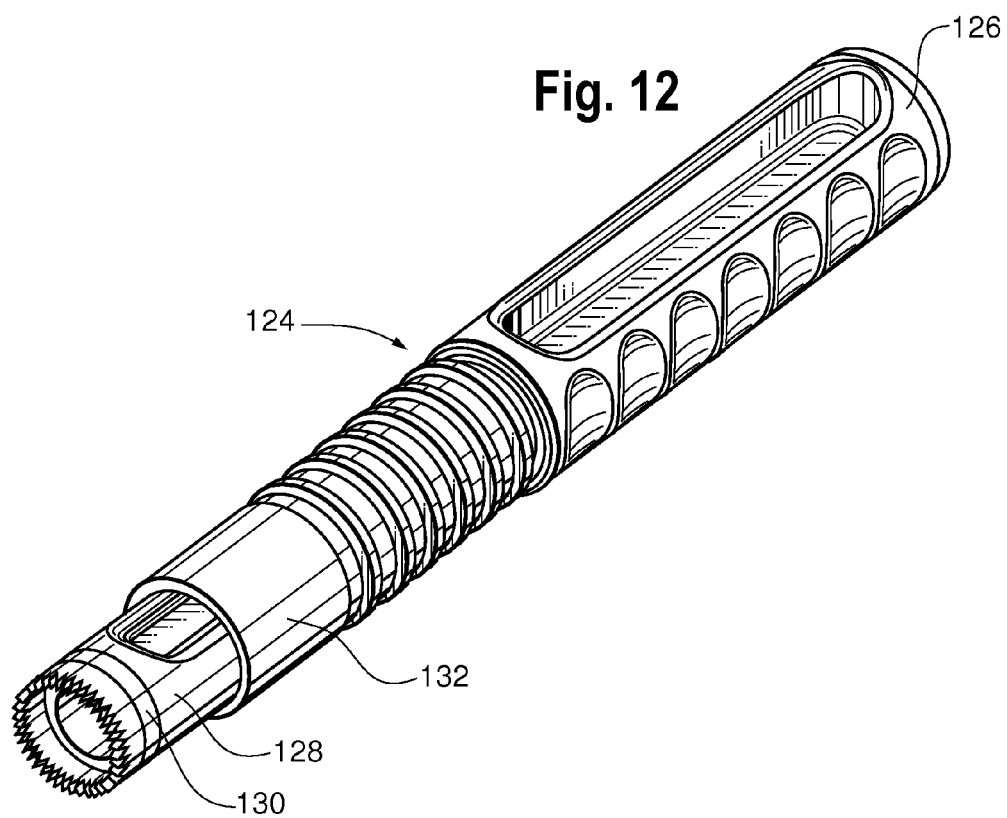
FIG. 12 is a perspective view of a tissue push tool for use in assembling and using the combination of stapler, buttress material, and tissue.

Using the present invention, abutting tissue portions can be held in place without the use of sutures. Composite buttress materials are particularly amenable to this approach, as the use of dissimilar materials enables a more rigid positioning region (50) to be used. One or more retention rings, as shown in FIG. 10, can be used to hold tissue in place over the reinforcing regions of buttress materials. In a preferred embodiment, these one or more retention rings can include the anvil retention ring (120) and the cartridge retention ring (122). A tissue push tool (124) has been created to assist in securely positioning the retention rings so that they retain the cut tissue ends against the reinforcing buttress materials during the stapling procedure. An embodiment of this tool is illustrated in FIG. 12. For use with a circular stapler, a cylinder-shaped tool shape is preferred. The tissue push tool (124) comprises a handle (126) which is used to manually maneuver the tool, a retaining ring support section (128), a retaining ring groove (130), and retaining ring release (132). The retaining ring support section (128) bears a retaining ring, which is held in place in the retaining ring groove (130).

Figure 13:
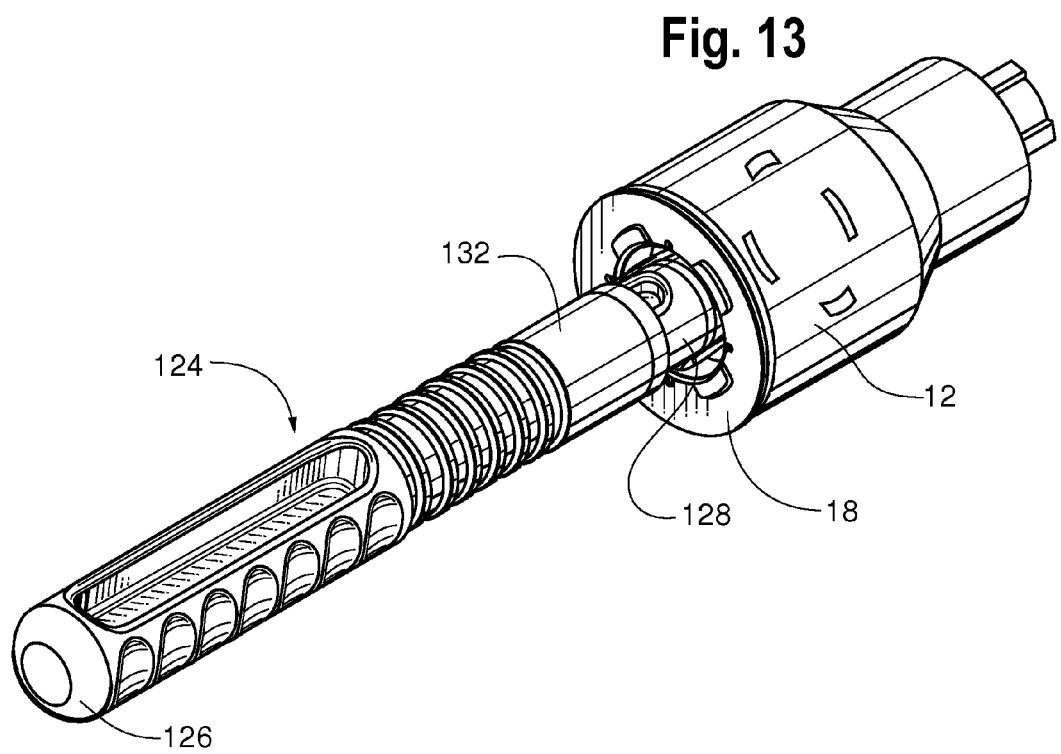
FIG. 13 is a perspective view of a tissue push tool inserted into a stapler cartridge.

Once the retaining ring, supported by the tissue push tool (124), has been placed over tissue positioned over buttress material, the retaining ring release (132) may be pushed down towards and past the retaining ring groove (130) so that the retaining ring is released from the tool and positioned to hold the tissue in place. The tissue push tool (124) is shown inserted into a stapler cartridge component (12) in FIG. 13 to help illustrate its use. Preferably, the tissue push tool (124) is used once and discarded. Examples of polymeric materials suitable for use in the tissue push tool (124) include one or more polymeric materials selected from the group consisting of polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof. In one preferred embodiment, the tissue push tool is constructed using polyethylene.

A buttress material of the present invention can be positioned over corresponding stapler components prior to or following assembly of the anvil and staple components. Apart from positioning of the buttress material, the overall operation of fastening device is well known in the art and described in several patents, such as commonly assigned U.S. Pat. Nos. 4,576,167, 5,005,749, and 5,119,983. Except where noted otherwise, the materials utilized in the components of the surgical instrument generally include such materials as polycarbonate for housing sections and related components, and stainless steel for the anvil assembly and components which transmit forces. However, equivalent alternative materials will readily come to the mind of those skilled in the art.

In other aspects, the invention provides a kit for preparing a combination as described herein, as well as a buttress material, per se, adapted for such use, a method of preparing such a buttress material, and a method of performing a surgical stapling procedure using such a material and combination.

It will be understood that various modifications may be made to the embodiments disclosed herein. For example, the use of buttress material on a circular stapler with a pivoting fastener head instead of a rigidly attached fastener head would be well within the invention disclosed in the present application.

Circular stapler buttress material in one embodiment is fabricated from a homogenous biomaterial, typically bovine pericardium sheet, which has been shaped by fixing it upon a preformed shape using a tanning solution. The actual buttress portions used are defined by the shapes of the components they are adapted to be positioned upon, which for a circular stapler are typically the staple cartridge and anvil components. The cartridge buttress includes a biomaterial preformed by fixing upon a template and trimming to form a disc with a central cylindrical depression with a hole at its base, which snugly fits on the staple-firing end of the staple cartridge. The anvil buttress includes a biomaterial preformed by fixing upon a template and trimming to form a ring-shaped disk with an incurvate central lip which fits snugly on the anvil-plate end of the anvil.

With regard to buttress materials of the present invention, in particular the homogenous buttress material, it has been discovered that certain natural animal tissues, properly preserved and processed, present superior properties for preformed buttress materials. In particular, it has been found that if the buttress materials are pre-formed in a shape corresponding to the shape of respective stapler components, and the tissue processed or cross-linked, a superior buttress is produced which facilitates the stapling procedure. In particular, bovine pericardial tissue has been used quite successfully. Cross-linked tissue is preferred for homogenous buttress materials, as it provides the desired physical and biological characteristics. Cross-linked tissue may also be used in composite buttress materials, but non-crosslinked material is preferred for composite buttresses. The preparation of non-crosslinked material is described in detail further below. Both processed buttress materials of the invention are sterile and can be readily situated and attached in place. They can be produced in all convenient sizes required.

Homogenous buttress materials may be formed from pre-soaked or dehydrated animal tissue using shaping forms of desired configurations and sizes. The shaping forms are covered with the buttress material which is secured in place in a manner that provides both a generally planar portion adapted to be positioned on either the cartridge or anvil face, respectively, and an interior non-planar portion adapted to be positioned within the annular aperture of such components. Either prototype stapler devices or tailor-made forms (e.g., mandrels) designed to mimic the size and configuration of the particular stapler can be used as shaping forms It will be appreciated that a preferred process for manufacturing homogenous buttress materials in the preformed, cross-linked state in accordance with the process of the present invention results in a superior and more successful material. A flow chart describing the process for manufacturing circular stapler homogenous buttresses using pericardium in accordance with the invention is shown in FIG. 5.

In accordance with the invention, it has been found that certain natural animal tissues, properly preserved and processed, possess superior properties when used as buttress materials, particularly if manufactured in a preformed shape. In particular, bovine pericardial tissue has been used quite successfully. It will be recognized, however, that while the processes and products are described herein with particularity to the use of bovine pericardial tissue, that is intended by way of example and not limitation inasmuch as it is believed that other suitable materials can be similarly processed.

In accordance with the manufacture of homogenous buttress materials of the present invention, it is important to obtain high quality starting material. The starting material is obtained from slaughtered animals and it is necessary to preserve the condition of the harvested animal tissue. As shown at (70) in FIG. 5, the preferred starting material is raw bovine pericardial tissue. This tissue must meet certain minimum standards and is generally harvested from United States Department of Agriculture (USDA) inspected cattle that are at least one year old, which have been processed by selected slaughterhouses. The harvesting should occur within two hours of slaughter and the harvested tissue must be of a minimum size in order to be useful for processing into the materials of the invention. The harvested sacs are placed in ice water immediately after collection and the water/saline solution is frequently changed to remove residual blood. The tissue is thereafter packaged in containers which maintain a temperature in the range of 32°-55° F. (2-5° C.) and shipped to arrive for processing, preferably within 72 hours after collection.

Figure 5B:
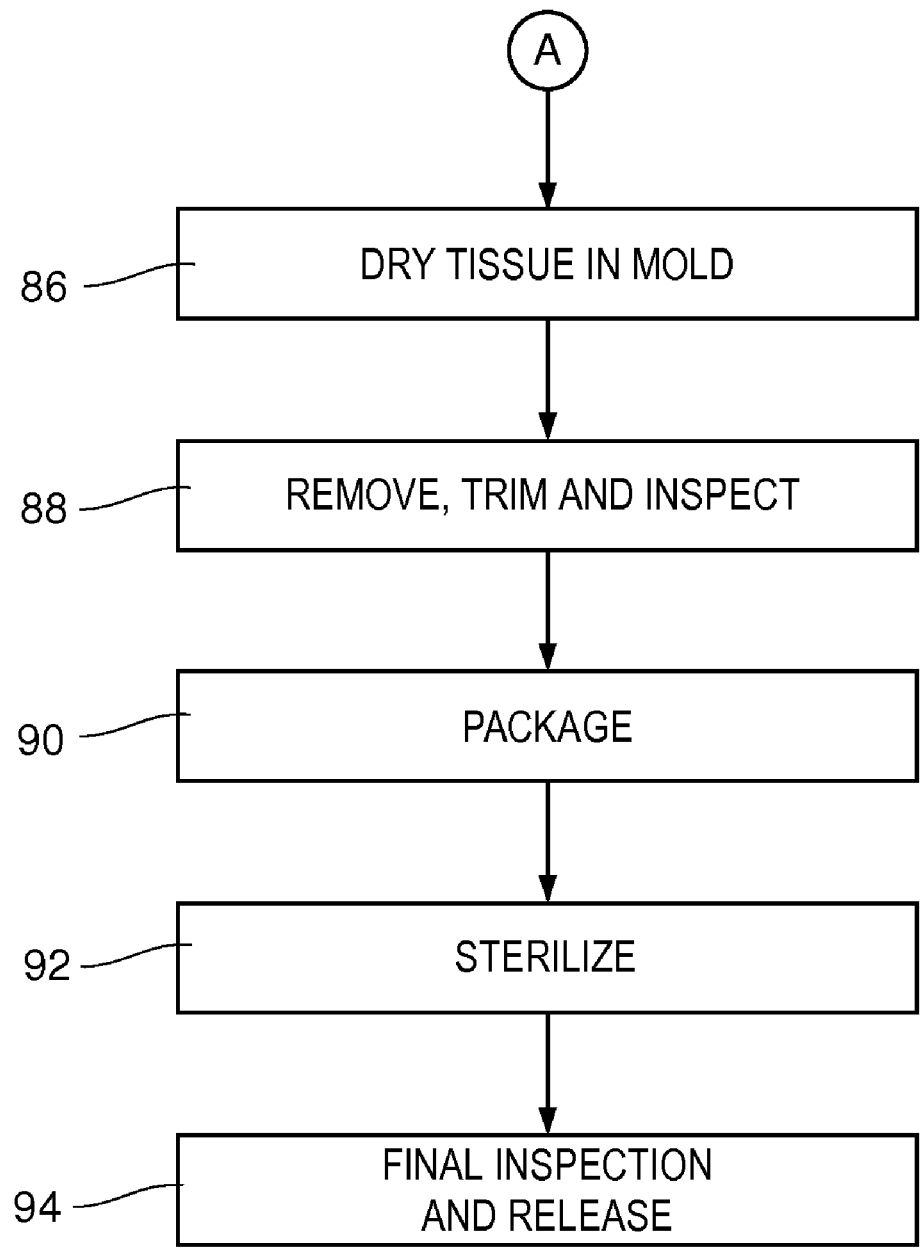
Figure 6A:
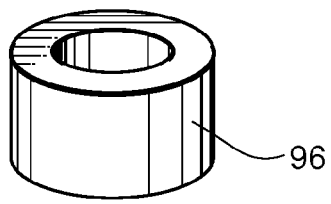
FIG. 6 is a schematic view in perspective illustrating the technique for preparing a portion of homogenous buttress material.
Figure 6B:
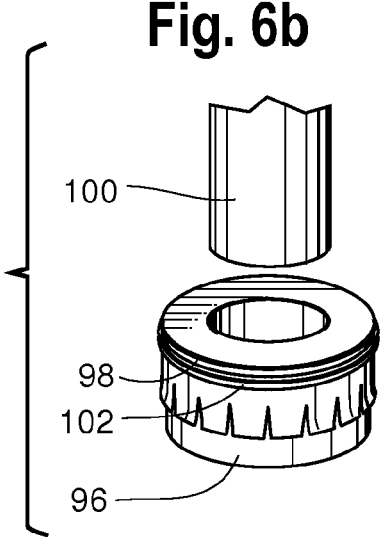
Figure 6C:
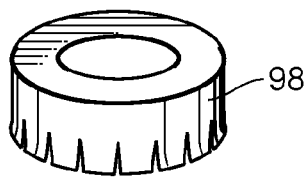
Figure 6D:
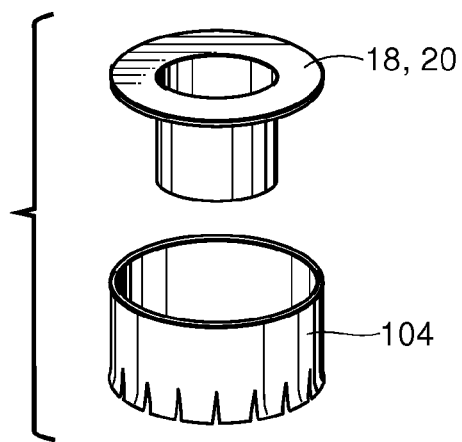

Incoming raw pericardium is initially tested and inspected (72) as shown in FIG. 5 and in accordance with a raw pericardium testing and inspection procedure that includes inspection of the material in a controlled environment for size, discoloration, environmental debris or parasites, cuts or tears (that would not afford a minimum area for use) and thickened, rough fatty or fibrous tissue. Certificates of origin and other documents are verified. The tissue is then ready for further processing.

Pericardial tissue is then subjected to a plurality of saline rinses at (74) utilizing isotonic saline. The rinses are performed in order to leach away any residual blood, and the minimum soaking time for each rinse should be approximately 30 minutes. In the case of frozen tissue, the series of cold isotonic saline rinses normally includes 2-5 rinses. If fresh tissue is used, usually 1-3 isotonic saline rinses suffice. More rinses may be used, in either case, if necessary, to remove all of the blood.

At this point in the process, a quality assurance or quality control bioburden test is performed on samples of the material to assure that the maximum bioburden is not exceeded by the material. Typically, the bioburden needs to be less than $1.0 \times 10^8$ CFU/gram of sac tissue. This is based on a randomly selected sample of approximately 10 grams representing material from each control number batch. These tests are conducted in a well-known manner. Once the quality of the material has been assured, step (76) is conducted wherein the material is cut to the appropriate size (eg. 8 cm×8 cm) for shaping into buttress material. The material is die cut using a mounted knife edge of the appropriate dimensions.

Initial crosslinking of the tissue is then performed. In the pre-soak (78), the cut, raw, isotonic saline-rinsed bovine pericardial tissue is transferred to trays containing approximately 0.25% glutaraldehyde solution for a minimum of 5 minutes but no longer than about 15 minutes prior to covering. After 5 minutes and before 15 minutes in the approximate 0.25% glutaraldehyde solution, the tissue, which has a shiny, visceral or inside surface and a dull, parietal or outside surface, is removed and placed on a cutting board where it is again inspected for holes, thick or thin areas, or peeling or freezer burned areas. Any extraneous tissue is cleared away from both sides of the pericardial tissue at this time. Tissue will be further crosslinked once placed upon a shaping device.

Pre-forming of the material is now undertaken (80). In this part of the process, bovine pericardial tissue is covered around a suitable shaped device for the purpose of shaping the tissue prior to further processing. This is illustrated in detail in FIG. 6. For example, a prototype was made was made using a medium density foam with an outer diameter of 24 mm and an inner diameter of 18 mm as the shaping device, as illustrated in step 1 of FIG. 6 (96). The dimensions of the material should approximate those of the stapler components for which the buttress material is intended.

A single sheet of cut pericardial material (98) should then be placed evenly over the shaping device (96), as shown in the second step of FIG. 6. A short segment of plastic tubing (100) (e.g., with an outer diameter of 17 mm) is then used to force the pericardium into the foam template to a depth of approximately 1 cm. A rubber band (102) is then placed to hold the edges of the pericardium against the outer surface of the foam template. Wrinkles in the buttress surface are removed by manual smoothing, taking care not to stretch the tissue or force the plastic tubing (100) out of the central hole.

The tissue-covered form is placed in a lyophilizer vessel filled with enough 0.25% glutaraldehyde solution to cover the fixtures. A vacuum is pulled briefly to evacuate the air from the fixture and to replace it with 0.25% gluteraldehyde solution. The foam has been suitably affected by the vacuum when the tissue covered foam assemblies sink in the solution of 0.25% gluteraldehyde.

For gluteraldehyde tanning (82), the tissue covered form is placed in a fixation tank containing 0.25% gluteraldehyde solution. After al tissue-covered forms are placed in the tank, additional 0.25% gluteraldehyde is added to insure that all covered forms are fully immersed. The covered forms are allowed to remain in the gluteraldehyde solution at room temperature for a minimum of 48 hours and a maximum of 96 hours prior to removal.

The tissue-covered form is then placed in a lyophilizer vessel filled with enough deionized (DI) water to cover the fixtures (84). A vacuum is pulled briefly to force DI water into the foam. The fixture containing tissue is then transferred back to the fixation vessels containing DI water for 15-120 minutes.

If it is to be used dry, the now chemically fixed tissue is then vacuum dried while on the form and the tissue is subsequently removed from the form (86). The dried, separated pericardium (98) is shown in FIG. 6. The tissue is then placed face down, support ring up, and circularly cut evenly about the support ring to the desired diameter (88). The diameter is dictated by outer diameter of desired intraluminal stapler. This results in a formed portion of buttress material (18/20) and excess cut-away pericardial tissue (104) which is discarded. The tissue is then placed upon a mounting device and packaged (90) prior to sterilization via e-beam (92).

If used wet, the now chemically fixed tissue is removed from the form. The tissue is then placed face down (support ring up) and circularly cut evenly about the support ring to the desired diameter. The diameter is dictated by outer diameter of desired intraluminal stapler. The tissue can then placed upon a mounting device if required. The tissue is treated with a solution of 70% ethanol, 1% propylene oxide for 48 to 432 hours. After the initial 70% ethanol, 1% propylene oxide treatment, tissue can be inspected and stored thereafter in jars filled with 70% ethanol, 1% propylene oxide for 75 hours minimally.

Thereafter the tissue is subjected to another quality inspection. The jarred tissue is drained and refilled with fresh 70% ethanol, 1% propylene oxide for 14 days minimally. After this step, a quality assurance sterility check is conducted during which the 70% ethanol, 1% propylene oxide is drained and the inspected tissue is immersed in sterile water containing 1% propylene oxide. Alternatively to this procedure, the tissue can be terminally sterilized with γ-irradiation, which decreases the required number of ethanol-containing solution changes. The caps are torqued in accordance with established procedures. A quality inspection is conducted. Finally, the package is labeled and the final inspection and release to stores is conducted (94).

Non-crosslinked tissue for use in the present invention can be obtained from any suitable source including mammalian sources, e.g., in the form of collagenous connective tissue with three dimensional intertwined fibers. As noted, non-crosslinked material is used to form the reinforcing portion (48) in a preferred embodiment of the composite buttress material. Such tissues generally include serous and fibro-serous membranes. In a particularly preferred embodiment, the tissue source is selected from bovine pericardium, peritoneum, fascia lata, dura mater, derinis, and small intestinal submucosa. In a further preferred embodiment, the tissue is bovine pericardium, and is treated using a method as described herein to provide the treated tissue with an optimal combination of biocompatability, thickness, and other physical and physiological properties.

Tissues for preparation of non-crosslinked material can be provided from dura mater, for instance, for use in neurosurgical applications. Collagenous connective tissue with three dimensional intertwined fibers, when treated in the manner described herein, retains the multidirectional and mechanical strength of native dura matter, while providing the basic formative structure to support replacement by new endogenous tissue.

While it is desirable to reduce or eliminate antigenic properties of xenografic or even allografic tissue-based material to be implanted into a body, if the body's absorption and/or remodeling of the material are desired, crosslinking should be avoided. In order to specifically perform such modification of a collagen-based material, a monofunctional reagent is therefore used. The reagent is "monofunctional" in that it is adapted to react with, and therefore terminate or "cap" the available amine functionalities of tissue proteins, but will not further react with adjacent groups. An optimal reagent of this invention, therefore, is preferably a relatively small and structurally simple compound that, upon reaction with protein groups such as amines, will bind to those groups but will not otherwise alter the biological properties of the collagen matrix to an extent that renders the tissue unsuitable for its intended use.

In a particularly preferred embodiment, a tissue of the present invention is treated by a process that includes alkylating a major percentage of its available amine groups to an extent sufficient to permit the tissue to be implanted and used in vivo. Preferably a tissue is processed by alkylating its amines to an extent sufficient to react 80% or more, preferably 90% or more, and most preferably 95% or more of the amine groups originally present. The efficacy and extent of alkylation can be determined by a variety of means, as described herein, including the use of a ninhydrin-based assay ("amine index") to determine a comparative level of amine groups, before and after treatment (see, e.g., Sung H-W, et al. Art Org., 21: 50-58; 1997. Sung, H-W, et al., J. Biomed. Mater. Res. 33: 177-186. 1996). Preferably the efficacy and extent of the alkylation process is further assessed by determining unreacted amounts in the batch incubation of the alkylating agent used.

Preferred alkylating agents can be used, for instance, at a pH of between about 9 and about 11, and at a concentration of between about 2% (v/v) and about 5% (v/v), by exposing the tissue to a solution containing the agent for at least 48 hours.

Preferred alkylating agents include small and reactive amine alkylating agents, such as formaldehyde, and 1,2-epoxy compounds. The epoxy agents offer an advantage over formaldehyde in that they tend to produce more stable adducts in their reactions with amines (Sung, H-W., et al., Biomater., 17: 2357-2365; 1996). 1,2-epoxy agents can react with a primary amine at alkaline pH to produce an extremely stable 2-hydroxy secondary amine. However, an aldehyde such as formaldehyde reacts with a primary amine to produce a marginally unstable, reversible double-bonded aldimine (Girardot, J-M. and Girardot, M-N., J. Heart Valve Dis., 5: 518-525; 1996).

Of the various monofunctional 1,2-epoxy agents, propylene oxide ("PO") is particularly preferred since it possesses properties that render its inclusion into a material process simple, yet effective. Propylene oxide (epoxypropane) has been used for several years as a sterilant, mostly in a gaseous state, although at room temperature, it exists as a liquid (Hart, A. and Brown, W., Appl. Microbiol., 28: 1069-1070; 1975). Many years ago, PO was revealed to directly modify carboxylic, thiol, phenolic and amine groups of proteins under certain conditions (Fraenkal-Conrat, H., J. Biol. Chem., 154: 227-

238; 1944). As has been demonstrated with other epoxides, propylene oxide reacts predominantly with amines at alkaline pH. Collagen swells at alkaline pH rendering it more accessible to be alkylated with a water-soluble agent such as propylene oxide.

Another preferred monofunctional epoxy reagent for use in the present invention is methyl glycidyl ether, as is produced by the Nagase Corp. of Osaka, Japan and sold under the product name Denacol® EX-131. This product has a low molecular weight, is water-soluble and was shown to be a more potent alkylating agent for porcine pericardium than formaldehyde (Sung, H-W., et al., J. Biomed. Mater. Res., 35: 147-155; 1997).

In a preferred embodiment, a tissue of the present invention is also treated with a base such as sodium hydroxide (NaOH), in order to further lessen the already minimal possibility of Bovine Spongiform Encephalopathy (BSE) transmission. Histological analyses of NaOH-treated tissue (pericardium, for example) reveals virtually complete decellularization due to this treatment. Since the cellular component of tissue is known to contain the vast majority of the antigen load (Courtman, D. W., et al., J. Biomed. Mater. Res., 28: 655-666; 1994), decellularization treatment with NaOH can complement the use of an alkylating agent in reducing antigenicity.

In a preferred embodiment, a process of preparing non-crosslinked material includes the steps of:
 a) obtaining pericardium from a suitable (e.g., USDA-approved) source,
 b) cleaning the tissue and optionally, and preferably, treating the tissue, e.g., in order to decellularize it and/or to reduce/eliminate potential BSE infectivity,
 c) alkylating the tissue (e.g., hydroxypropylation using propylene oxide) to cap a major percentage of available (e.g., potentially reactive) amine groups, and optionally,
 d) final processing, including one or more of the following steps: washing, drying, sterilizing and packaging the tissue.

EXAMPLES

Example 1

Roux-En-Y Gastric Bypass Procedure Using Circular Stapler Buttress Material

The surgical steps to create a Roux-en-Y gastric bypass using circular stapler buttress material are as follows. After the institution of general endotracheal anesthesia, a nasogastric tube and catheter are placed. Pneumatic sequential compression devices are applied to the lower extremities. The patient is given 2,500 units of low-molecular weight heparin and an intravenous dose of ampicillin/sulbactam. Trocars are then placed in the umbilicus and various ports. A "Y" connector is attached to the insufflator to allow for carbon dioxide insufflation through two trocars.

The stomach is approached through the gastrohepatic ligament and transected with a 45-mm endoscopic linear stapler such as those manufactured by Ethicon Endo-Surgery, (Cincinnati, Ohio), leaving a 15 to 20 cc gastric pouch. The patient is placed in steep Trendelenherg's position, and the greater omentum and transverse colon are reflected caudally. The jejunum is transected with an endoscopic stapler approximately 25 cm to 40 cm distal to the ligament of Trietz. The mesentery is split vertically with ultrasonic coagulating shears. The Roux (distal jejunum) limb is then passed to the esophageal hiatus.

Circular buttress material is applied to a circular stapler of any diameter. The anvil and cartridge of the circular stapler are separated. The circular buttress is then introduced to the anvil and the cartridge and is pressed into place so that the buttress lies flat against each stapler component "face". A viscous gel (e.g. a standard gel as available under the tradename "PSD Gel" from Synovis Life Technologies, Inc.) may be applied prior to positioning to enhance retention of the buttress on the stapler during manipulation in the body. Alternatively, a pressure-sensitive adhesive may be deposited on the buttress as a part of the manufacturing process in place of gel application by the end-user. The anvil buttress and cartridge buttress are then mated to the anvil and cartridge of the stapler, respectively. Following attachment of the buttress material, the anvil may be reattached to the cartridge and closed onto a foam support in order to enhance the adhesion between buttress and stapler. After an appropriate period of compression, the anvil is then opened, the anvil and foam support (if used) are removed, and the stapler is then ready to use.

For this procedure, a small (<25 mm) "flip top" circular stapler is used to allow for the safe, antegrade passage of the larger anvil through the esophagus. The flip top of the stapler anvil is flipped. A suture is passed between the top of the flipped anvil and the small hole in the tip of the anvil's post and tied. After the flip top is secured into the flipped position, the distal (larger) end of a nasogastric tube is transected just proximal to its air or sump port. The stapler's anvil will fit snugly into the lumen of the cut nasogastric tube at this point. A silk stitch is used to secure the anvil in the nasogastric tube by passing the needle and suture through one side of the tube, through the small hole in the anvil's post, and out the other side of the tube. The suture is then tied to itself to secure the anvil within the nasogastric tube.

The nasogastric tube and anvil are coated with a sterile water-soluble lubricant, and the proximal nasogastric tube is positioned into the gastric pouch. When the tip of the proximal nasogastric tube reaches the staple line of the gastric pouch, a 4-mm gastrotomy is made over the tip of the nasogastric tube with laparoscopic scissors, and the tube is pulled into the abdomen. The nasogastric tube is slowly advanced and pulled out through one of the lower abdominal trocars. As the tube is slowly pulled into the abdomen, the anvil is guided through the oropharynx under direct vision via a laryngoscope. Once in the esophagus, the stapler head of the anvil slides down easily into position in the gastric pouch. After the tip of the anvil has passed through the gastrotomy, the sutures holding the anvil in the nasogastric tube and flip top of the anvil are cut. The anvil is advanced until the flip top returns to its normal perpendicular position. To further facilitate removing the anvil from the nasogastric tube, the tube where the post is inserted is split with a harmonic scalpel. This instrument quickly cuts through the plastic, allowing the nasogastric tube to be pulled free and out to the abdomen. Alternatively, the anvil may be introduced into the gastric pouch laproscopically via a hole made in the pouch using a harmonic scalpel. This allows a larger stapler (>26 mm) to be used.

The staple line of the Roux jejunal limb is excised with the harmonic scalpel. The fastener head of the stapler is introduced directly through the abdominal wall. The stapler passed into the opening in the Roux jejunal limb and then several centimeters distally. The post of the anvil protruding through the gastric pouch is locked onto the fastener head. The anastomosis is stapled in the standard fashion by carefully positioning the tissue and firing the stapler. The positioning portion(s) of the buttress are cut from the buttress portions after firing the stapler. This remnant material, as well as circular portions of the small bowel and pouch, are then removed from the patient along with the stapler. It is customary for the surgeon to inspect the condition of the tissue "rings" for integrity, as this is an indication of a circumferential anastomosis. At this point remnant buttress material can be discarded along with the used stapler.

The open end of the Roux limb is then closed with an endoscopic linear stapler. The Roux-en-Y enteroenterostomy is created 60 cm to 100 cm distal to the gastrojejunal anastomosis with an endoscopic linear stapler using standard laparoscopic anastomotic techniques. Prior to closing the trocar sites, the gastrojejunal anastomosis is tested with methylene blue infused through a nasogastric tube that will remain postoperatively.

Example 2

Creation of a Colorectal Anastomosis Using Circular Stapler Buttress Material

Circular staplers are also used in colorectal surgery to create a leak-proof anastamosis between large intestine and the rectum. This procedure can also be improved through the use of circular stapler buttress material. As in the previous example, buttress material is positioned on the anvil and cartridge components and pressed into place so that the buttress lies flat against each stapler "face". A viscous gel of the type described above may be applied prior to positioning to enhance retention of the buttress on the stapler during manipulation in the body. Alternatively, a pressure sensitive adhesive may be deposited on the buttress as a part of the manufacturing process in place of gel application by the end-user. Following attachment of the buttress material, the anvil is reattached to the cartridge and closed onto a foam support in order to enhance the adhesion between buttress and stapler. After an appropriate period of compression, the anvil is then opened, the anvil and foam support (if used) are removed, and the stapler is then ready to use.

In colorectal surgery, the distal fastener head is usually inserted through the anus. In most instances, the maneuver is facilitated using a Fansler or Chelsey-Eaton anoscope which allows gradual, controlled dilation of the anal sphincter muscles. After removal of the obturator, the stapler shaft can easily be passed through the anoscope. Once through the sphincter, the stapler must be inserted up to the resected end of the rectum. The anvil is positioned into the resected end of the large intestine. The shaft of the anvil extends beyond the end of the intestine with a purse-string suture holding tissue in place.

The anvil and cartridge of the stapler are connected and the stapler is closed and fired. Positioning portions of the buttress are cut from the buttress upon firing of the stapler. This remnant material as well as circular portions of the large bowel and rectum are removed from the patient along with the stapler. The integrity of the anastomosis is then assessed as in Example #1.

What is claimed is:

1. A combination medical device comprising: a) a circular stapler instrument, comprising a staple cartridge component and corresponding anvil component, and b) a buttress adapted to be a) stably positioned upon the staple cartridge and/or anvil components of the stapler prior to, or at the time of, use, b) while in position upon the stapler component(s), to then be delivered to a tissue site in combination with the stapler components, c) upon delivery of the components and positioned buttress to the tissue site, to provide a first region of buttress material to buttress a seam between tissue sections upon activation of the stapler instrument, and d) to permit the removal of one or more portions of a second region upon activation of a stapler instrument knife provided by the stapler, the second region being generally concentric to the first region and wherein the first region and the second region are formed of dissimilar materials.

2. The combination according to claim 1 wherein the first region comprises preformed animal tissue.

3. The combination according to claim 2 wherein the preformed animal tissue comprises pericardium.

4. The combination according to claim 3 wherein the pericardium has been formed by a process that includes the steps of forming the pericardium onto a mandrel or other model shape, soaking the formed pericardium in a crosslinking solution, removing the pericardium from the mandrel or other model shape, and sterilizing the pericardium.

5. The combination according to claim 1 wherein the buttress is provided as a plurality of portions, including one portion adapted to fit the staple cartridge and another portion adapted to fit the anvil component.

6. The combination according to claim 1, the first and second regions cooperating to provide a desired three dimensional and/or topographic structure adapted to position and/or retain the buttress in place upon the respective stapler component.

7. The combination according to claim 1 wherein the first region comprises animal tissue and the second region comprises a polymer.

8. The combination according to claim 1 wherein the first region comprises non-crosslinked, mammalian tissue.

9. A method of performing a surgical stapling procedure, the method comprising the steps of providing a combination according to claim 1, and employing the stapler and buttress to provide a buttressed surgical seam between joined tissue portions.

10. The method according to claim 9 wherein the first region comprises preformed animal tissue.

11. The method according to claim 10 wherein the preformed animal tissue comprises pericardium.

12. The method according to claim 11 wherein the pericardium has been formed by a process that includes the steps of forming the pericardium onto a mandrel or other model shape, soaking the formed pericardium in a crosslinking solution, removing the pericardium from the mandrel or other model shape, and sterilizing the pericardium.

13. The method according to claim 9 wherein the buttress is provided as a plurality of portions, including one portion adapted to fit the staple cartridge and another portion adapted to fit the anvil component.

14. The method according to claim 9, the first and second regions cooperating to provide a desired three dimensional and/or topographic structure adapted to position and/or retain the buttress in place upon the respective stapler component.

15. The method according to claim 14 wherein the first region comprises animal tissue and the second region comprises a polymer.

16. The method according to claim 14 wherein the first region comprises non-crosslinked, mammalian tissue.

17. The method according to claim 9 wherein the buttressed surgical seam is created without first binding said abutting tissue portions with one or more sutures.

18. The method according to claim 9 wherein one or more retaining rings are used to help retain the tissue on the buttress.

19. The method according to claim 18 further including the step of using a tissue push tool to place the one or more retaining rings.

20. The combination of claim 1, wherein the second region comprises a frustoconical shape.

21. The combination of claim 20, wherein the cone of the frustoconical shape comprises a plurality of petals.

22. A kit for use in a circular stapling procedure employing a circular stapler that comprises a staple cartridge component and a corresponding anvil component, the kit comprising a buttress adapted to be a) stably positioned upon the staple cartridge and/or anvil components of the stapler prior to, or at the time of, use, b) while in position upon the stapler component(s), to then be delivered to a tissue site in combination with the stapler components, c) upon delivery of the components and positioned buttress to the tissue site, to provide a first region of buttress material to buttress a seam between tissue sections upon activation of the stapler instrument, and d) to permit the removal of one or more portions of a second region upon activation of a stapler knife provided by the stapler, the second region being generally concentric to the first region and wherein the first region and the second region are formed of dissimilar materials.

23. The kit according to claim 22 wherein the first region comprises preformed animal tissue.

24. The kit according to claim 23 wherein the preformed animal tissue comprises pericardium.

25. The kit according to claim 24 wherein the pericardium has been formed by a process that includes the steps of forming the pericardium onto a mandrel or other model shape, soaking the formed pericardium in a crosslinking solution, removing the pericardium from the mandrel or other model shape, and sterilizing the pericardium.

26. The kit according to claim 22 wherein the buttress is provided as a plurality of buttress portions, including one portion adapted to fit the staple cartridge and another portion adapted to fit the anvil component.

27. The kit according to claim 22, the first and second regions cooperating to provide a desired three dimensional and/or topographic structure adapted to position and/or retain the buttress in place upon the respective stapler component.

28. The kit according to claim 22 wherein the first region comprises animal tissue and the second region comprises a polymer.

29. The kit according to claim 28 wherein the first region comprises non-crosslinked, mammalian tissue.

30. A method of forming a buttress for use in a kit according to claim 22, the method comprising the steps of treating the first region positioned upon a form of suitable size and shape to approximate that of a surgical stapler component.

31. The method according to claim 30 wherein the first region comprises preformed animal tissue.

32. The method according to claim 31 wherein the preformed animal tissue comprises pericardium.

33. The method according to claim 32 wherein the pericardium has been formed by a process that includes the steps of forming the pericardium onto a mandrel or other model shape, soaking the formed pericardium in a crosslinking solution, removing the pericardium from the mandrel or other model shape, and sterilizing the pericardium.

34. A method of forming a buttress portion for use in a kit according to claim 22, the method comprising the steps of preparing a plurality of portions, including one portion adapted to fit the staple cartridge and another portion adapted to fit the anvil component.

35. The method according to claim 34, the, first and second regions cooperating to provide a desired three dimensional and/or topographic structure adapted to position and/or retain the buttress in place upon the respective stapler component.

36. The method according to claim 35 wherein the first region comprises animal tissue and the second region comprises a polymer.

37. The method according to claim 36 wherein the first region comprises non-crosslinked, mammalian tissue.

38. The method according to claim 37 further including the step of attaching the first region to the second region by welding, friction, adherence, tacking, or tongue-in-groove attachment.

39. A circular stapler buttress comprising a buttress adapted to be a) stably positioned upon at least one stapler component of a circular stapler prior to, or at the time of, use, b) while in position upon the stapler component(s), to then be delivered to a tissue site in combination with the stapler component(s), c) upon delivery of the stapler components and positioned buttress to the tissue site, to provide a first region of buttress material as a staple line buttress seal between joined tissue sections upon activation of the stapler, and d) to permit the removal of a second region of the buttress material upon activation of a stapler knife provided by the stapler, the second region being generally concentric to the first region and wherein the first region and the second region are formed of dissimilar materials and the second region comprises a frustoconical shape.

40. The circular stapler buttress of claim 39, wherein the circular stapler buttress is adapted to be stably positioned on a staple cartridge component.

41. The circular stapler buttress of claim 39, wherein the circular stapler buttress is adapted to be stably positioned on a staple anvil component.

42. The circular stapler buttress of claim 39 wherein the first region comprises tissue in the form of sterilized pericardium, the first and second regions cooperating to provide a desired three dimensional and/or topographic structure adapted to position and/or retain the buttress upon the stapler cartridge component.

43. The circular stapler buttress of claim 42 wherein the first and second regions are adapted to be separated upon activation of a stapler knife, in a manner sufficient to permit the separated first region to provide a buttressed surgical seam between joined tissue portions and to permit the separated second region to be removed from the tissue site.

\* \* \* \* \*